US012569211B2

(12) United States Patent
Sato et al.

(10) Patent No.: US 12,569,211 B2
(45) Date of Patent: Mar. 10, 2026

(54) X-RAY DIAGNOSTIC APPARATUS AND IMAGE PROCESSING METHOD

(71) Applicant: CANON MEDICAL SYSTEMS CORPORATION, Otawara (JP)

(72) Inventors: Daisuke Sato, Utsunomiya (JP); Yoshimasa Kobayashi, Nasushiobara (JP); Katsuo Takahashi, Utsunomiya (JP); Suzuna Saito, Nasushiobara (JP); Takahiro Tanaka, Nasushiobara (JP); Katsunori Kojima, Hadano (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 169 days.

(21) Appl. No.: 18/534,886

(22) Filed: Dec. 11, 2023

(65) Prior Publication Data

US 2024/0197274 A1    Jun. 20, 2024

(30) Foreign Application Priority Data

Dec. 16, 2022    (JP) ................................. 2022-201381

(51) Int. Cl.
| | |
|---|---|
| *A61B 6/00* | (2024.01) |
| *A61B 6/04* | (2006.01) |
| *A61B 6/42* | (2024.01) |
| *A61B 6/46* | (2024.01) |
| *G06T 7/00* | (2017.01) |

(52) U.S. Cl.
CPC .......... *A61B 6/5205* (2013.01); *A61B 6/0487* (2020.08); *A61B 6/4208* (2013.01); *A61B 6/463* (2013.01); *G06T 7/0012* (2013.01)

(58) Field of Classification Search
None
See application file for complete search history.

(56) References Cited

U.S. PATENT DOCUMENTS

| | | | | |
|---|---|---|---|---|
| 2017/0322484 A1* | 11/2017 | Erhard | .................. | A61B 6/467 |
| 2018/0116613 A1 | 5/2018 | Von Berg et al. | | |
| 2019/0183439 A1* | 6/2019 | Joerger | .................. | A61B 6/545 |
| 2023/0404495 A1 | 12/2023 | Brueck et al. | | |

FOREIGN PATENT DOCUMENTS

| | | |
|---|---|---|
| EP | 4 000 525 A1 | 5/2022 |
| JP | 2017-536860 A | 12/2017 |

OTHER PUBLICATIONS

Extended European Search Report Issued Apr. 26, 2024 in European Application 23217047.2, citing documents 1-3 & 15 therein, 8 pages.

* cited by examiner

*Primary Examiner* — Hoon K Song

(74) *Attorney, Agent, or Firm* — Oblon, McClelland, Maier & Neustadt, L.L.P.

(57) ABSTRACT

In one embodiment, an X-ray diagnostic apparatus comprising: an X-ray tube configured to irradiate an imaging part of an object with X-rays; an X-ray detector configured to detect the X-rays; an image sensor configured to image the object; and processing circuitry configured to acquire: a human body model; image data from the image sensor; and imaging geometry information, detect positioning of the object from the image data, set the human body model based on detected positioning of the object, generate a predicted X-ray image that is predicted to be detected by the X-ray detector, by using the set human body model and the imaging geometry information, and display the predicted X-ray image.

20 Claims, 14 Drawing Sheets

CAMERA IMAGE OBTAINED BY IMAGE SENSOR S

DETECT ACTUAL POSITIONING OF OBJECT

POSITIONING INFORMATION

HUMAN BODY MODEL

PREDICTED X-RAY IMAGE THAT HAS BEEN SUBJECTED TO VIRTUAL POSITIONING

X-RAY DIAGNOSTIC APPARATUS AND IMAGE PROCESSING METHOD

CROSS-REFERENCE TO RELATED APPLICATION

This application claims the benefit of priority of Japanese Patent Application No. 2022-201381, filed on Dec. 16, 2022, the entire contents of which are incorporated herein by reference.

FIELD

Disclosed embodiments relate to an X-ray diagnostic apparatus and an image processing method.

BACKGROUND

In X-ray image diagnosis, it is necessary to acquire an X-ray image that accurately depicts an imaging part as the target of diagnosis or treatment. In the following, the term "imaging part" refers to an X-ray data acquisition range defined as an anatomical site of a human body such as the head and the chest of an object or a patient, for example.

Due to difference in experience between users such as a medical imaging technologist, there are cases where a desired imaging part cannot be accurately imaged. In particular, there are cases in which plain radiography using X-ray imaging with specific positioning is desired for follow-up observation of disease and/or injury such as fracture in clinical departments such as orthopedics, but this positioning may not be achieved due to the orientation of the object with respect to the X-ray imaging direction and the various positional relationships of respective parts of the object.

To image the object such as a patient with clinically appropriate positioning in X-ray image diagnosis, though it is effective to adjust the object to the appropriate positioning during preliminary imaging or during X-ray fluoroscopy, there is a problem that the radiation exposure increases. There is also a known method in which a camera image of the imaging part of the object is acquired and then the outer shape of the clinically ideal positioning in accordance with the examination purpose is superimposed on this camera image in order to prompt the object to change its positioning to the ideal one, which enable reduction in the radiation exposure. However, even if the positioning of the object is changed so as to match the ideal one, the actual acquired X-ray image may remain unclear, and the user has to predict what the X-ray image may show on the basis of conditions such as the posture of the object and the positional relationship between bones and/or organs, and re-imaging may be required in some cases depending on difference in skill and experience between users.

DETAILED DESCRIPTION

Hereinbelow, embodiments of an X-ray diagnostic apparatus and an image processing method will be described in detail by referring to the accompanying drawings.

In one embodiment, an X-ray diagnostic apparatus comprising: an X-ray tube configured to irradiate an imaging part of an object with X-rays; an X-ray detector configured to detect the X-rays; an image sensor configured to image the object; and processing circuitry configured to acquire: a human body model; image data from the image sensor; and imaging geometry information, detect positioning of the object from the image data, set the human body model based on detected positioning of the object, generating a predicted X-ray image that is predicted to be detected by the X-ray detector, by using the set human body model and the imaging geometry information, and display the predicted X-ray image.

First Embodiment

Figure 1:
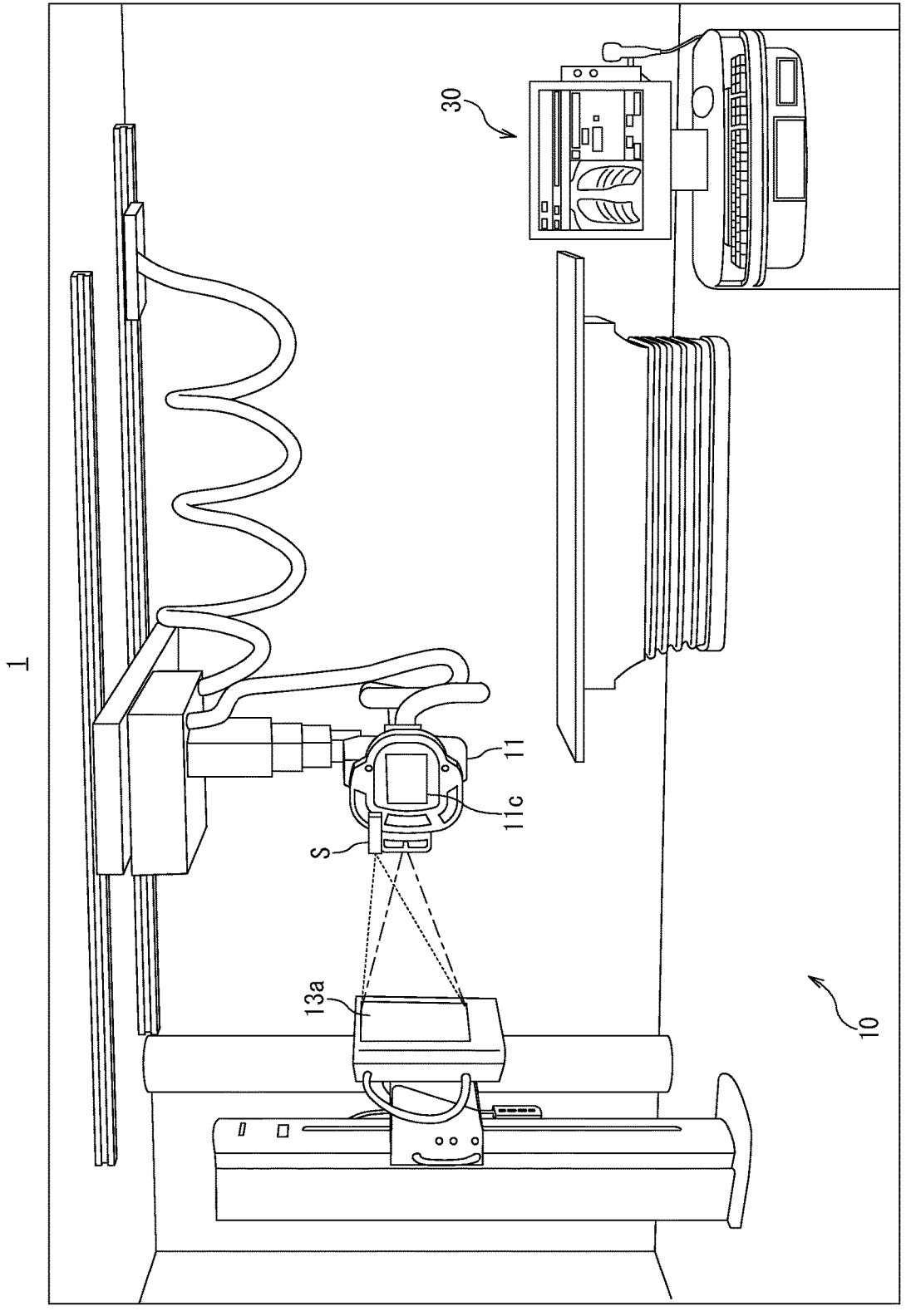
FIG. 1 is a perspective view illustrating appearance of a part of an X-ray diagnostic apparatus according to the first embodiment.
Figure 2:
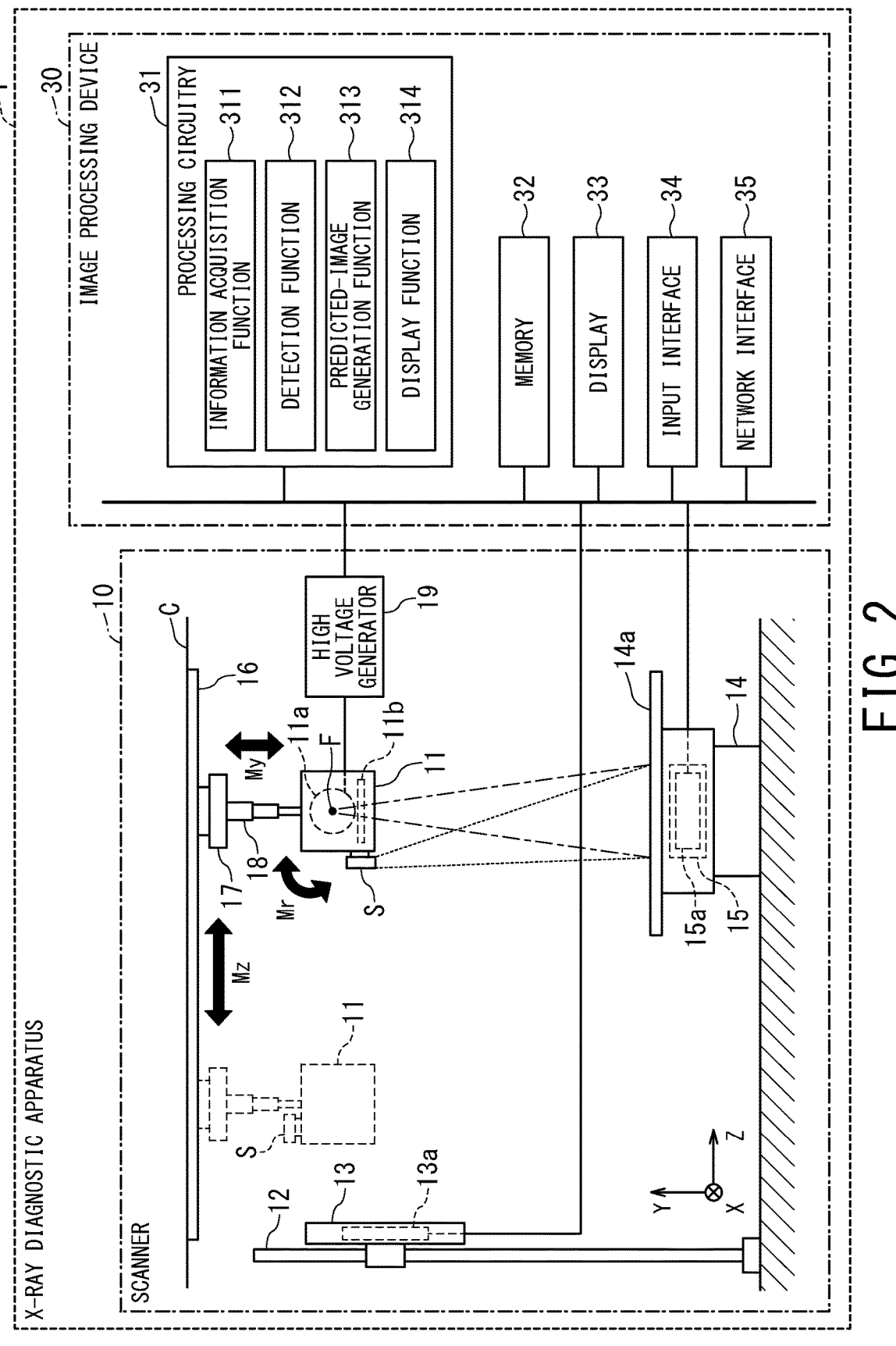
FIG. 2 is a schematic diagram illustrating a configuration of the X-ray diagnostic apparatus according to the first embodiment.

FIG. 1 is a perspective view illustrating appearance of a part of an X-ray diagnostic apparatus 1 according to the first embodiment. FIG. 2 is a schematic diagram illustrating a configuration of the X-ray diagnostic apparatus 1 according to the first embodiment. Aspects of the X-ray diagnostic apparatus 1 include, for example, a plain X-ray apparatus such as an X-ray radiography apparatus.

As shown in FIG. 1 and FIG. 2, the X-ray diagnostic apparatus 1 according to the first embodiment includes a scanner 10 and an image processing device 30 (for example, a console 30).

The scanner 10 includes a tube holder 11, an upright-position examining table 12, an upright-position detector unit 13, a bed 14, a decubitus-position detector unit 15, a ceiling rail 16, a carriage 17, a supporting column 18, a high voltage generator 19, and an image sensor S. As shown in FIG. 2, the height direction of the upright-position examining table 12 is defined as the Y-axis direction, the left-right direction of the object standing on the upright-position examining table 12 is defined as the X-axis direction, and the direction orthogonal to both the X-axis direction and the Y-axis direction is defined as the Z-axis direction.

The tube holder 11 holds an X-ray tube 11*a*, an X-ray variable aperture 11*b*, and an operation panel 11*c*. The X-ray tube 11*a* receives power supply from the high voltage generator 19 and radiates X-rays to the imaging part of the object placed in front of the upright-position examining table 12 or placed on the bed 14.

The X-ray variable aperture 11*b* is composed of a plurality of aperture blades, for example. Each of the aperture blades is composed of a tabular lead blade to shield X-rays, for example. The region surrounded by the plurality of aperture blades forms an aperture through which X-rays pass.

The operation panel 11*c* is composed of, for example, a liquid crystal display, and is attached to the outer wall of the tube holder 11. The operation panel 11*c* can be configured by adapting a GUI (Graphical User Interface), which makes extensive use of graphics when displaying information on a display to a user and allows basic operations to be performed by using an input interface. The operation panel 11*c* can also display various images such as a camera image acquired by the image sensor S configured to image the object P as described below and display various information items such as information for assisting the user in positioning of the object P.

The tube holder 11 is engaged with the supporting column 18 so as to be able to rotate the tube holder 11 in the direction Mr around the axis (i.e., X-axis) that passes through the X-ray focal point F of the X-ray tube 11*a* and is orthogonal to the extension and contraction direction of the supporting column 18. Under the control of processing circuitry 31 of the image processing device 30, the X-ray tube 11*a* is rotatable within a range of −180° to +180° in the rotational direction around the X-axis, Y-axis, or Z-axis passing through the X-ray focal point F.

The image sensor S performs optical imaging and generates camera images or moving images under the control of the processing circuitry 31 of the image processing device 30. The imaging range of the image sensor S includes the range where the X-rays radiated to the imaging part of the object P are detected by the X-ray detector. At least one image sensor S is attached to the tube holder 11 holding the X-ray tube 11*a* at the same side from which the X-rays are emitted.

By having the image sensor S provided at the above-described position, the imaging range and imaging angle of the image sensor S can follow the X-ray irradiation range and the X-ray irradiation angle to the object P which are changed respectively in conjunction with the movement of the tube holder 11 holding the X-ray tube 11*a* and the rotation of the X-ray tube 11*a* around the X-ray focal point F. Furthermore, the image sensor S may be attached near the X-ray exit of the tube holder 11.

When there is one image sensor S that can perform imaging in the same direction as the X-ray irradiation direction, the actual positioning of the object P can be detected in two dimensions. Furthermore, when a plurality of image sensors S are provided and the same part of the object P is imaged by the plurality of image sensors S, the actual positioning of the object P can be three-dimensionally detected from the plurality of camera images by using the principle of a stereo camera, for example.

Aspects of the image sensor S include a camera such as a CCD (Charge Coupled Device) camera and a CMOS (Complementary Metal Oxide Semiconductor) camera and a TV camera. The image sensor S may be an infrared camera. When an infrared camera is used as the image sensor S, the physique of the object P, and the positioning such as posture of the object P, can be detected without being interrupted by examination clothes, for example.

The upright-position detector unit 13 is supported by the upright-position examining table 12 disposed vertically at a position facing the tube holder 11, which enables detection of X-rays from the X-ray tube 11*a*. The upright-position detector unit 13 changes its height along the upright-position examining table 12 in accordance with change in height of the tube holder 11 under the control of the processing circuitry 31 of the image processing device 30.

The upright-position detector unit 13 includes an upright-position FPD (Flat Panel Detector) 13*a* and an A/D (Analog to digital) conversion circuit (not shown), for example. The upright-position FPD 13*a* has two-dimensionally arranged detection elements and detects X-rays. The A/D conversion circuit converts the output signal of the upright-position FPD 13*a* into a digital signal. Further, a grid may be provided in front of the upright-position FPD 13*a*. The upright-position FPD 13*a* detects transmitted X-rays from the object P in the upright position by simple X-ray radiography, and outputs them to the image processing device 30 as image signals.

The bed 14 is used as a decubitus-position examination table that can hold the object P in the decubitus position or sitting position. The bed 14 is supported by the floor and has a table 14*a* on which the object P is placed. The table 14*a* can slide in the X-axis direction and in the Z-axis direction, move up and down in the Y-axis direction, and roll under the control of the processing circuitry 31 of the image processing device 30.

The decubitus-position detector unit 15 is supported by the bed 14. The decubitus-position detector unit 15 has the same structure and function as the upright-position detector unit 13 described above, except that the object P is not imaged in the upright position but in the decubitus or sitting position. The decubitus-position FPD 15*a* and the upright-position FPD 13*a* are both one of the X-ray detectors. The decubitus-position FPD 15*a* has the same structure and function as the upright-position FPD 13*a*, thereby in the description of the upright-position FPD 13*a*, the upright-position FPD 13*a* can be read as the decubitus-position FPD 15*a*.

The ceiling rail 16 is installed on a ceiling C.

The carriage 17 supports the tube holder 11 via the supporting column 18. The carriage 17 is movably engaged with the ceiling rail 16 in the direction Mz in parallel with the Z-axis along the ceiling rail 16. The carriage 17 is configured in such a manner that the tube holder 11 is movable between the side of the upright-position examining table 12 and the side of the bed 14 under the control of the processing circuitry 31 of the image processing device 30 or by manual control. In other words, the carriage 17 can change the distance (Source Image Receptor Distance: SID) between the X-ray tube 11*a* (X-ray focal point F) and the upright-position FPD 13*a*. The carriage 17 may be installed in such a manner that the carriage 17 can move not only in the direction Mz along the ceiling rail 16 but also in the direction parallel to the X-axis.

The supporting column 18, which is supported by the carriage 17, supports the tube holder 11 at its lower end. The supporting column 18 is engaged with the carriage 17 so as to be movable in the direction My parallel to the Y-axis. The supporting column 18 is telescopic along the direction My under the control of the processing circuitry 31 of the image processing device 30. In other words, the supporting column 18 can change the distance (SID) between the X-ray tube 11a (X-ray focal point F) and the decubitus-position FPD 15a.

The high voltage generator 19 can supply high voltage power to the X-ray tube 11a of the tube holder 11 under the control of the processing circuitry 31 of the image processing device 30.

The image processing device 30 is computer-based, controls the operation of the entirety of the X-ray diagnostic apparatus 1, and performs image processing on X-ray image data and a plurality of X-ray images acquired by the scanner 10, for example. The image processing device 30 includes the processing circuitry 31, a memory 32, a display 33, an input interface 34, and a network interface 35.

The memory 32 stores various programs to be executed by the processing circuitry 31, various data necessary for executing the programs, and/or X-ray images, for example. The memory 32 has a configuration including one or more storage media readable by the processor, such as a magnetic or optical storage medium, and a semiconductor memory, and may be configured in such a manner that part or all of the programs and data in these storage media are downloaded from the network via the network interface 35.

The display 33 is configured as a general display output device such as a liquid crystal display and an OLED (Organic Light Emitting Diode) display. Under the control of the processing circuitry 31, the display 33 displays various images such as an X-ray image and a camera image generated by the image sensor S that images the object P as well as various information items including information for assisting the user in positioning of the object P.

The input interface 34 includes an input circuit and at least one input device that can be operated by a user. The input device is achieved by a track ball, a switch, a mouse, a keyboard, a touch pad by which input operation is performed by touching its operation screen, a touch screen in which the display screen and the touch pad are integrated, a non-contact input device using an optical sensor, and a voice input device, for example. When the input device is operated by the user, the input circuit generates a signal in accordance with the operation, and outputs it to the processing circuitry 31.

The processing circuitry 31 includes a special-purpose or general-purpose processor, and implements various functions related to the image processing method described below through software processing in which the programs stored in the memory 32 are executed. In addition, the processing circuitry 31 integrally controls each component of the scanner 10. The processing circuitry 31 may be configured of hardware such as an ASIC (Application Specific Integrated Circuit) and a programmable logic device including an FPGA (Field Programmable Gate Array). The various functions described below can also be implemented by hardware processing using such hardware. Additionally, the processing circuitry 31 can implement the various functions described below by combining hardware processing and software processing.

As shown in FIG. 2, the processing circuitry 31 implements each of an information acquisition function 311, a detection function 312, a predicted-image generation function 313, and a display function 314. The information acquisition function 311 acquires a human body model, image data obtained from the image sensor S, and imaging geometry information. The detection function 312 detects the positioning of the object P from the image data. The predicted-image generation function 313 sets a human body model on the basis of the positioning of the object P detected by the detection function 312, and uses the human body model that has been subjected to setting and the imaging geometry information to generate a predicted X-ray image that is predicted to be detected by the X-ray detector. The display function 314 displays the predicted X-ray image.

Regarding the processing from imaging using the image sensor S to generation of the predicted X-ray image, its outline will be described by referring to the operation of the X-ray diagnostic apparatus 1 according to the first embodiment shown in FIG. 3 as one example.

Figure 3:
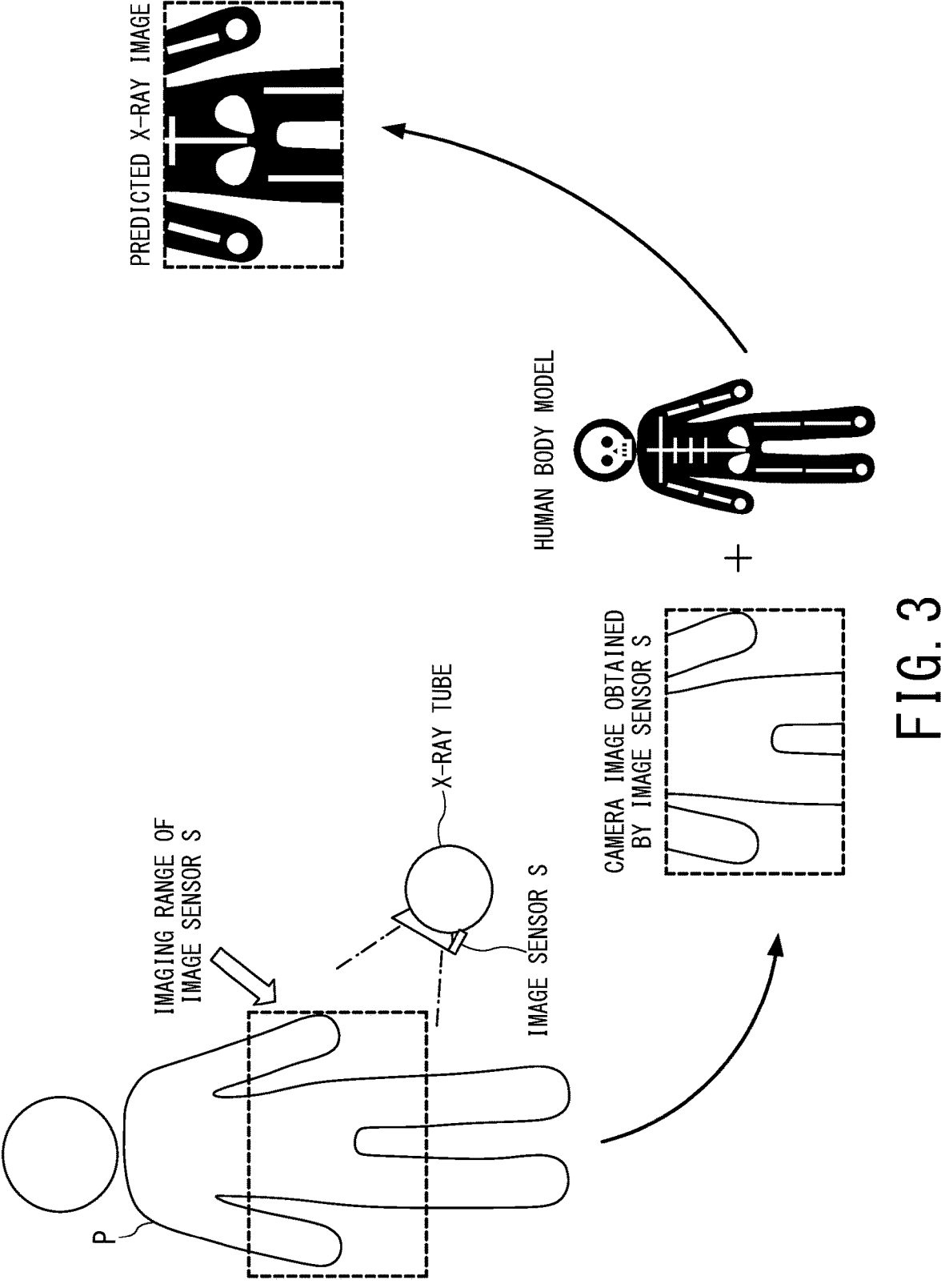
FIG. 3 is a schematic diagram illustrating operation of the X-ray diagnostic apparatus according to the first embodiment.

First, as shown in FIG. 3, the image sensor S is attached to the tube holder 11 in such a manner that allows the image sensor S to image the object P in the same direction as the X-ray irradiation direction, and then the imaging is performed to generate one or more camera images of the object P.

Next, on the basis of the positioning of the object P detected from at least one camera image that is acquired by the image sensor S, setting of the body parts of the human body model is performed. The processing for setting the human body model will be described below in detail.

The human body model is a three-dimensional human body model composed of digital data, which can be obtained via a portable recording medium and/or telecommunication lines such as the Internet, for example. The human body model includes at least the skeleton of a human body, and may also include organs and/or tissues such as blood vessels, internal organs, and muscles in addition to the skeleton.

The human body model may be configured in such a manner that each body part of the human body model moves from a reference position of a reference human body model on the basis of command information that gives instruction of a predetermined movement. For example, a user may provide the command information via the input interface 34 or the processing circuitry 31 may provide the command information. The human body model may be configured in such a manner that most body parts such as the head, the neck, the shoulders, the chest, the abdomen, the upper arms, the elbows, the forearms, the hands, the buttocks, the thighs, the knees, the lower legs, and the feet move on the basis of the command information. In other words, the human body model may be configured in such a manner that its posture or pose is changed on the basis of the command information. For example, the human body model may be configured in such a manner that (i) the skeleton of each body part is moved on the basis of the command information and in accordance with the natural movement of the object or person and (ii) the organs and tissues such as blood vessels, internal organs, and muscles are also moved in conjunction with the movement of the skeleton.

Figure 4:
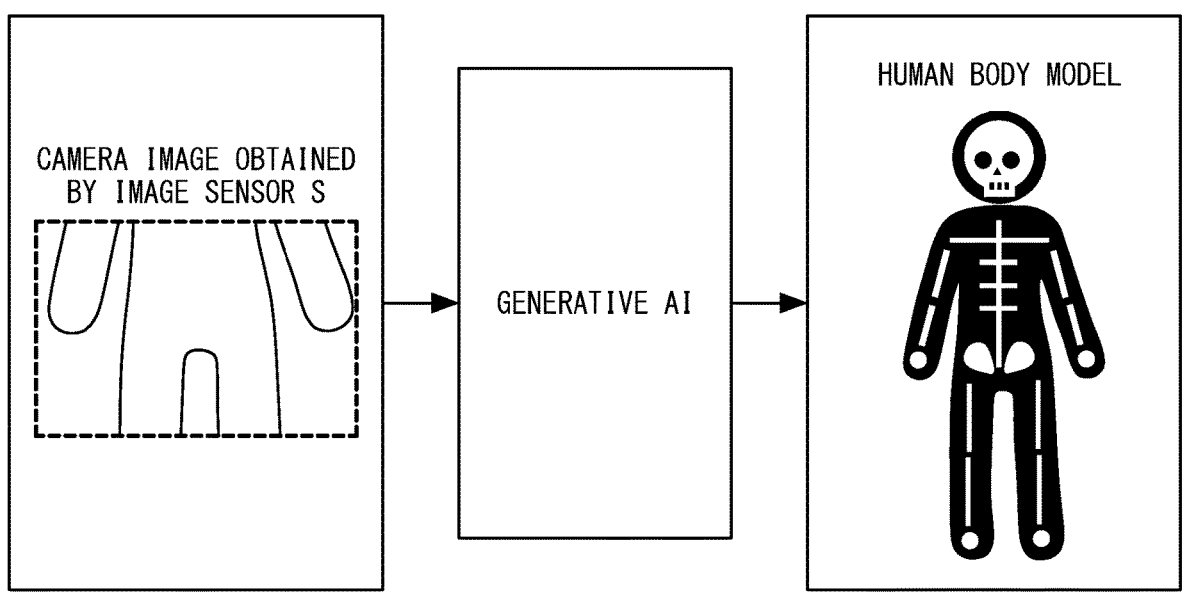
FIG. 4 is a schematic diagram illustrating a human body model according to the first embodiment.

In addition, the human body model may be a virtual human body model generated by Artificial Intelligence such as generative AI, or a known program. The generative AI is, for example, a machine learning model built by deep learning, which uses trained data to generate new data. FIG. 4 illustrates the human body model according to the first embodiment. As shown in FIG. 4, the generative AI is configured in such a manner that a human body model is outputted in response to input of a camera image generated by the image sensor S. In other words, the human body model may be generated by the generative AI in a customized or specialized manner on the basis of the positioning of the object P.

A two-dimensional image serving as the predicted X-ray image is generated on the basis of the imaging geometry information and the human body model that is set in the above-described manner. In other words, a predicted X-ray image is an image predicted to be generated when X-rays radiated to the imaging part of the object P are transmitted through this imaging part and detected by the X-ray detector, and is a two-dimensional image in which the human body model is virtually positioned.

The imaging geometry information means geometric information that defines the position and/or size of the object P in the X-ray image, such as the X-ray irradiation angle to the object P, the X-ray irradiation range to the object P, and the distance from the X-ray tube to the object P.

Next, the configuration and operation of each function of the processing circuitry 31 will be described in detail on the basis of the flowchart of FIG. 5 by referring to FIG. 6 and FIG. 7 as required. In each flowchart including FIG. 5, FIG. 9, FIG. 12, and FIG. 13, to facilitate understanding, the steps to be executed by the X-ray diagnostic apparatus 1 are shown in solid lines, whereas the steps based on an action and determination of a user are shown in broken lines.

In the step ST10, a user such as a medical imaging technologist performs initial positioning of the object P in such a manner that the desired imaging part of the object P is imaged. Since the step ST10 is an action and determination made by the user, the initial positioning of the object P may vary depending on difference in skill and experience between users.

In the step ST20A, the information acquisition function 311 acquires the human body model. The information acquisition function 311 can acquire appropriate one of the human body models stored in advance in the memory 32 or the human body model downloaded from the network via the network interface 35, for example. Aside from those, the information acquisition function 311 can acquire the human body model generated by the generative AI.

In the step ST30, the information acquisition function 311 acquires at least one camera image generated by the image sensor S.

In the step ST40, the information acquisition function 311 acquires the imaging geometry information including the X-ray irradiation angle to the object P.

In the step ST50, the detection function 312 detects the actual positioning of the object P from the camera image that is generated by the image sensor S and is acquired by the information acquisition function 311.

In the step ST60, the predicted-image generation function 313 virtually sets the body parts of the human body model acquired by the information acquisition function 311 in such a manner that the respective body parts correspond to the actual positioning of the object P detected by the detection function 312, and generates a virtually positioned predicted X-ray image, i.e., a predicted X-ray image in which virtual positioning is reflected.

Here, a description will be given of the detection of the actual positioning of the object P and the setting of the human body model according to the first embodiment by using FIG. 6. As shown in FIG. 6, for example, the actual positioning of the object P is detected by detecting the skeletal information such as a plurality of joints and facial parts of the object P from one or more camera images generated by the image sensor S.

Next, for example, the body parts of the three-dimensional human body model are moved on the basis of the imaging geometry information such as the X-ray irradiation angle to the object P, and are moved according to the actual positioning of the detected object P, such as the orientation of the body of the object P with respect to the X-ray exit port, the posture of the object P, and positional relationship between the respective body parts such as limbs. On the basis of the moved human body model and the imaging geometry information, a predicted X-ray image predicted to be generated when X-rays radiated to the imaging part of the object P are detected by the X-ray detector is then generated. In other words, on the basis of the moved human body model and the imaging geometry information, the predicted X-ray image is generated as a two-dimensional image of the human body model that has been subjected to virtual positioning so as to match the actual positioning of the object P.

In the step ST60, if the actual positioning of the object P matches the positioning of the human body model, the body parts of the human body model do not need to be moved. In other words, on the basis of the imaging geometry information and the human body model that has been subjected to setting, the predicted X-ray image predicted to be generated when X-rays radiated to the imaging part of the object P are detected by the X-ray detector is then generated.

Figure 6:
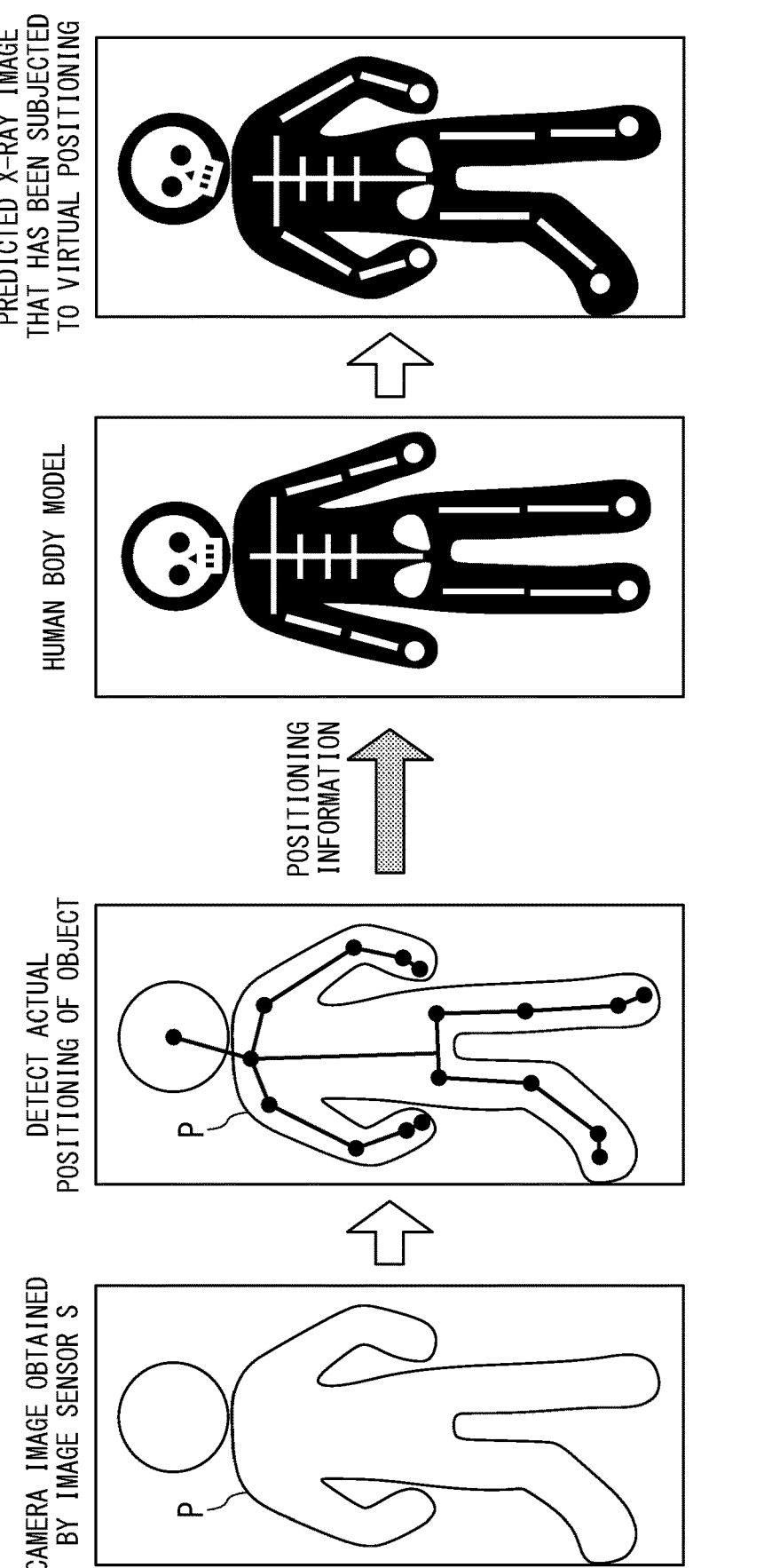
FIG. 6 is a schematic diagram illustrating positioning detection and setting of the human body model according to the first embodiment.

For convenience of description, FIG. 6 shows a situation where the entirety of the object P is detected by the image sensor S and the X-ray detector, rather than a specific part of the object P.

Returning to FIG. 5, in the step ST70, the display function 314 displays the predicted X-ray image generated by the predicted-image generation function 313. The predicted X-ray image is displayed on the operation panel 11c and/or the display 33, for example.

The display function 314 may change the display method of the predicted X-ray image depending on, for example, the imaging part and the examination purpose. For example, in the case of orthopedic diagnosis and treatment, a predicted X-ray image of only bones may be displayed. In the case of diagnosis and treatment in internal medicine and/or a gastrointestinal division where internal parts such as the abdomen are imaged, organs such as the liver, the kidneys, and the iliopsoas muscles may be displayed together with bones in the predicted X-ray image.

Figure 7C:
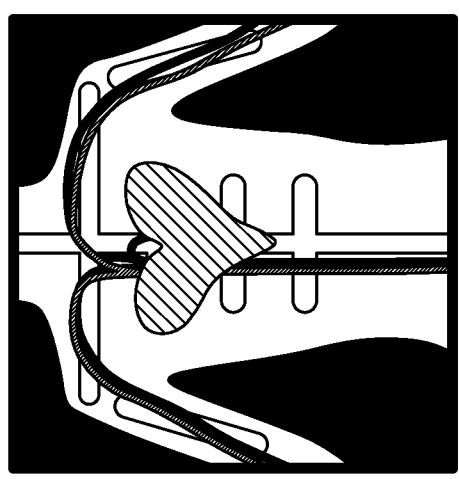
FIG. 7A to FIG. 7C are schematic diagrams illustrating predicted X-ray images according to the first embodiment.
Figure 7B:
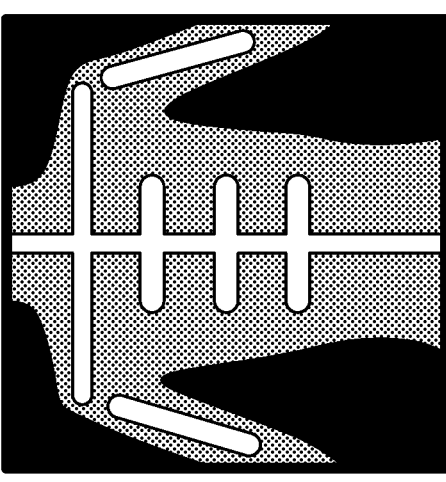
Figure 7A:
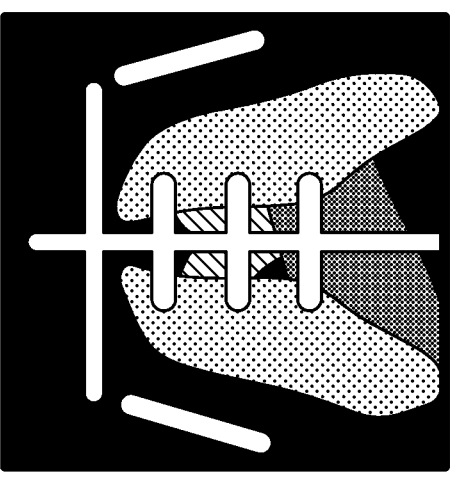

FIG. 7A to FIG. 7C are schematic diagrams illustrating predicted X-ray images according to the first embodiment. FIG. 7A illustrates a predicted X-ray image showing organs and bones, FIG. 7B illustrates a predicted X-ray image showing muscles and bones, and FIG. 7C illustrates a predicted X-ray image showing blood vessels and bones. In addition, the display function 314 may display semi-transparent bones or only the outlines of the bones in the predicted X-ray image.

The range of the predicted X-ray image to be displayed may be the same as the range of the actual X-ray radiographic image to be generated when the X-rays radiated to the imaging part of the object P are detected by the X-ray detector. Additionally or alternatively, the range of the predicted X-ray image to be displayed may be slightly wider than the range of the actual X-ray radiographic image so that an outline corresponding to the range of the actual X-ray radiographic is superimposed and displayed on the predicted X-ray image.

Returning to FIG. 5, in the step ST80, the user determines whether the displayed predicted X-ray image is as desired or not. If the user determines that the displayed predicted X-ray image is as desired (YES in the step ST80), under the state where the object P maintains its positioning, the X-ray diagnostic apparatus 1 images the object P. If the user determines that the displayed predicted X-ray image is not as desired (NO in the step ST80), the processing proceeds to the step ST100.

In the step ST100, the user performs repositioning of the object P. For example, the user may orally or visually instruct the object P on the position or the posture for the repositioning so that the predicted X-ray image to be displayed will be closer to the desired one in terms of positioning. Also in the step ST100, along with repositioning of the object P, the X-ray diagnostic apparatus 1 may adjust the placement of equipment and device such as the direction of the exit port of the X-ray tube 11a and the position of the X-ray detector under the control of the processing circuitry 31 in such a manner that the X-ray irradiation range and the irradiation angle become more appropriate for acquiring the desired predicted X-ray image.

After completion of the step ST100, the processing returns to the step ST30 in which the predicted X-ray image after repositioning is generated.

Figure 5:
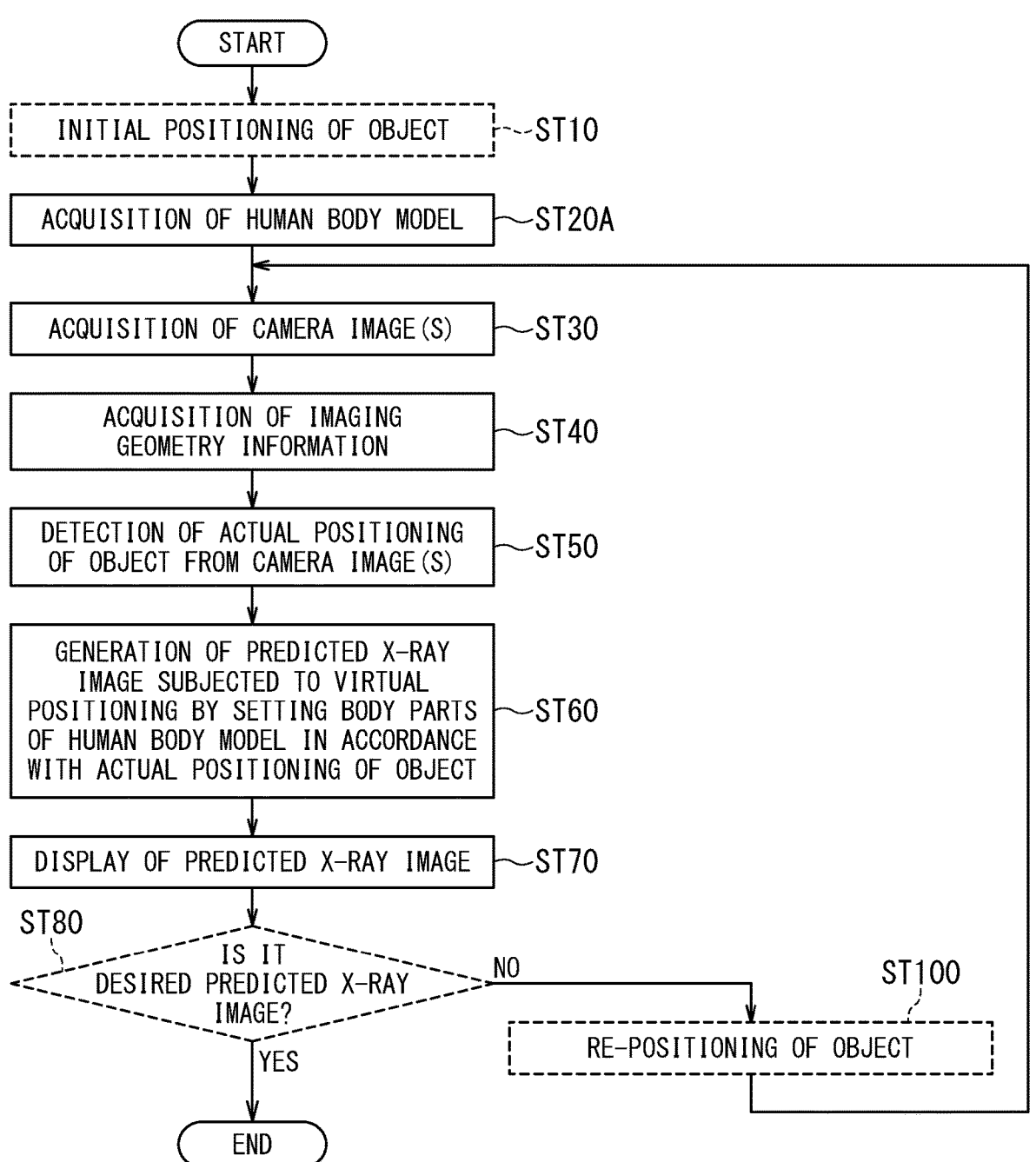
FIG. 5 is a flowchart illustrating operation of the X-ray diagnostic apparatus according to the first embodiment.

FIG. 5 illustrates the case of repeating the processing from the step ST30 to the step ST70 until the predicted X-ray image substantially matches the desired one in terms of positioning. However, if the user determines the desired predicted X-ray image can very likely be obtained after repositioning, the X-ray diagnostic apparatus 1 may perform X-ray imaging without returning to the step ST30.

According to the X-ray diagnostic apparatus 1 of the first embodiment, before performing an actual X-ray imaging, the user can check the predicted X-ray image that is generated based on the actual positioning of the object P from the camera image acquired by the image sensor S. This check can reduce the number of re-imaging due to inappropriate positioning of the object P caused by difference in skill and experience between users. Further, the addition of the simple configuration of the image sensor S enables assistance in repositioning the object P without increasing radiation dose.

Modification of First Embodiment

Figure 8:
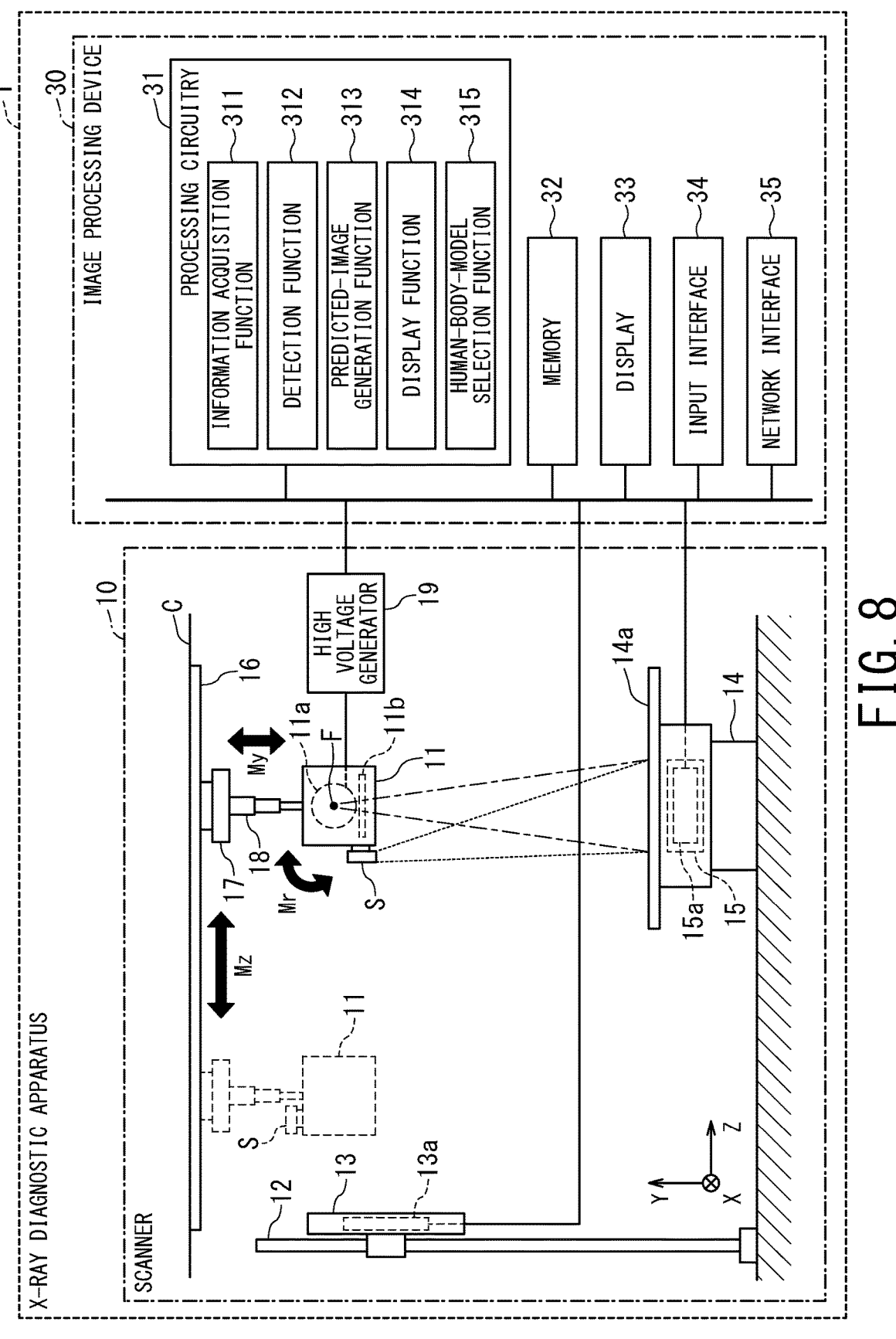
FIG. 8 is a schematic diagram illustrating a configuration of the X-ray diagnostic apparatus according to a modification of the first embodiment.
Figure 9:
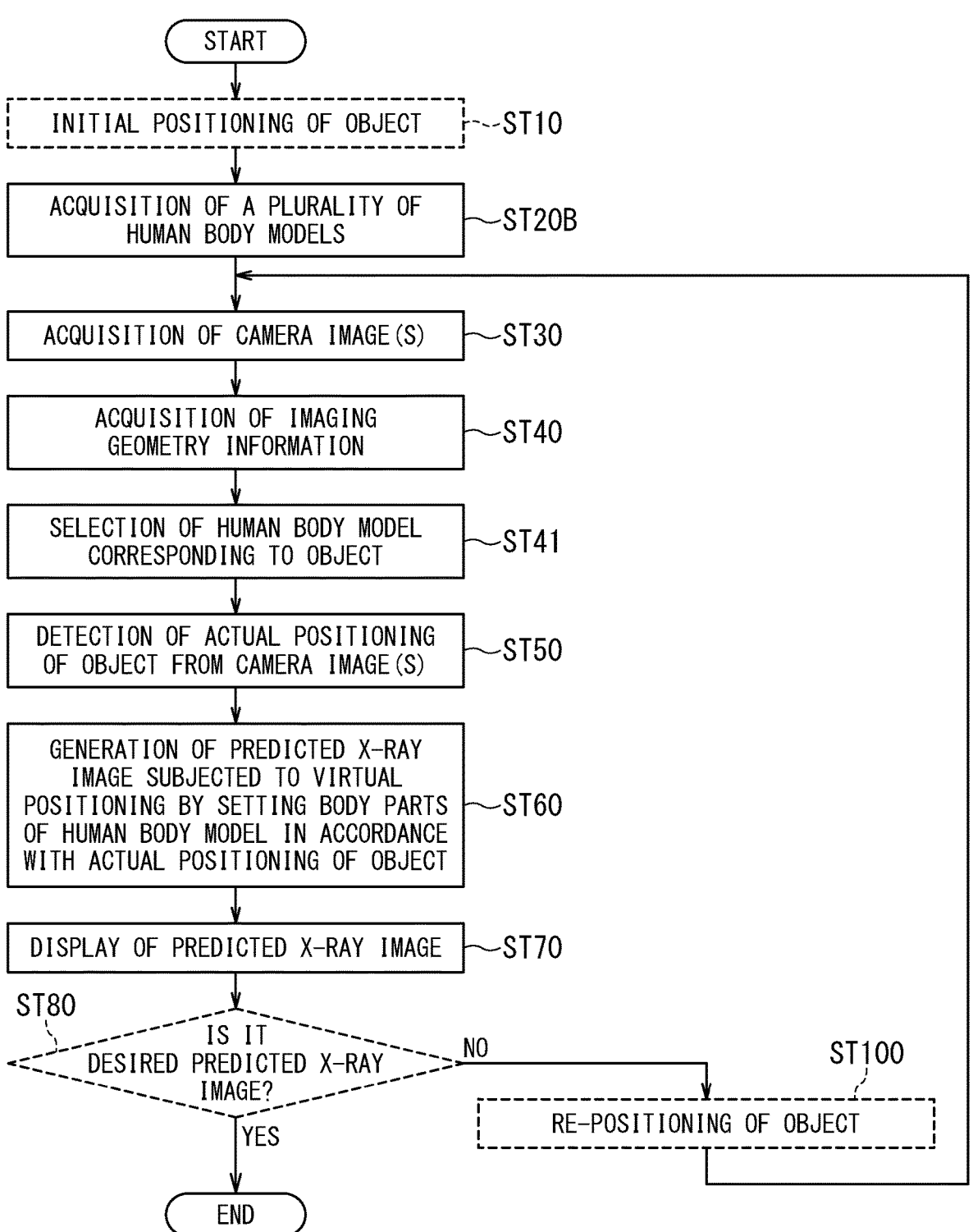
FIG. 9 is a flowchart illustrating operation of the X-ray diagnostic apparatus according to the modification of the first embodiment.

FIG. 8 is a schematic diagram illustrating a configuration of the X-ray diagnostic apparatus 1 according to a modification of the first embodiment. As shown in FIG. 8, the modification of the first embodiment differs from the first embodiment in that the processing circuitry 31 is further provided with a human-body-model selection function 315. FIG. 9 is a flowchart illustrating operation of the X-ray diagnostic apparatus 1 according to the modification of the first embodiment.

As shown in FIG. 9, the modification of the first embodiment differs from the first embodiment in that a plurality of human body models are acquired in the step ST20B and processing of selecting one human body model from the plurality of human body models is performed in the step ST41, whereas only one human body model is acquired in the first embodiment. Since the rest of the configurations and operation are not substantially different from that of the X-ray diagnostic apparatus 1 shown in FIG. 2, the same reference signs are given to the same configurations, and duplicate description is omitted. The same steps as those in FIG. 5 are denoted by the same reference signs, and duplicate description is omitted.

In the step ST20B, the information acquisition function 311 acquires a plurality of human body models. Each of the plurality of human body models is a three-dimensional model including the skeleton of the human body. Each human body model may contain organs and tissues such as blood vessels, internal organs, and muscles. In addition, the information acquisition function 311 can acquire the plurality of human body models from the human body models stored in advance in the memory 32 and the human body models downloaded from the network via the network interface 35, for example.

The plurality of human body models to be acquired in the step ST20B include, for example, a human body model with a standard body shape for each gender and each age and another human body model with a characterized body shape in terms of skeleton or physique. The human body model with the characterized body shape in terms of skeleton or physique means a human body model that is limited to a special range of values of at least one of its skeleton parameters such as height, weight, sitting height, shoulder width, hip width, and limb length as well as its physique parameters such as flesh consists of organs and tissues. Further, the plurality of human body models may be human body models generated from medical diagnostic images such as CT images and MRI images that are acquired in the past. Additionally or alternatively, the plurality of human body models may be, for example, a plurality of human body models that are different in positioning from each other. The information acquisition function 311 may be configured to be able to acquire human body models that are different in positioning depending on the type of diagnosis and treatment.

The processing from the step ST30 to the step ST40 is the same as the processing in the first embodiment (FIG. 5).

In the step ST41, the human-body-model selection function 315 selects one human body model from the plurality of acquired human body models.

It is preferred that one human body model to be selected from the plurality of human body models is a human body model having a close physical resemblance to the skeleton or physique of the object P. Further, one human body model to be selected from the plurality of human body models is preferably a human body model generated from medical diagnostic images such as a CT image and an MRI image that are generated by imaging the same object P in the past. If a human body model that is more similar to the skeleton or physique of the object P or the human body model of the object P oneself is selected, a more accurate predicted X-ray image can be generated. Additionally, one human body model to be selected from the plurality of human body models may be a human body model having similar positioning of the object P.

The processing from the step ST50 to the step ST70 is the same as the processing in the first embodiment (FIG. 5).

Figure 10:
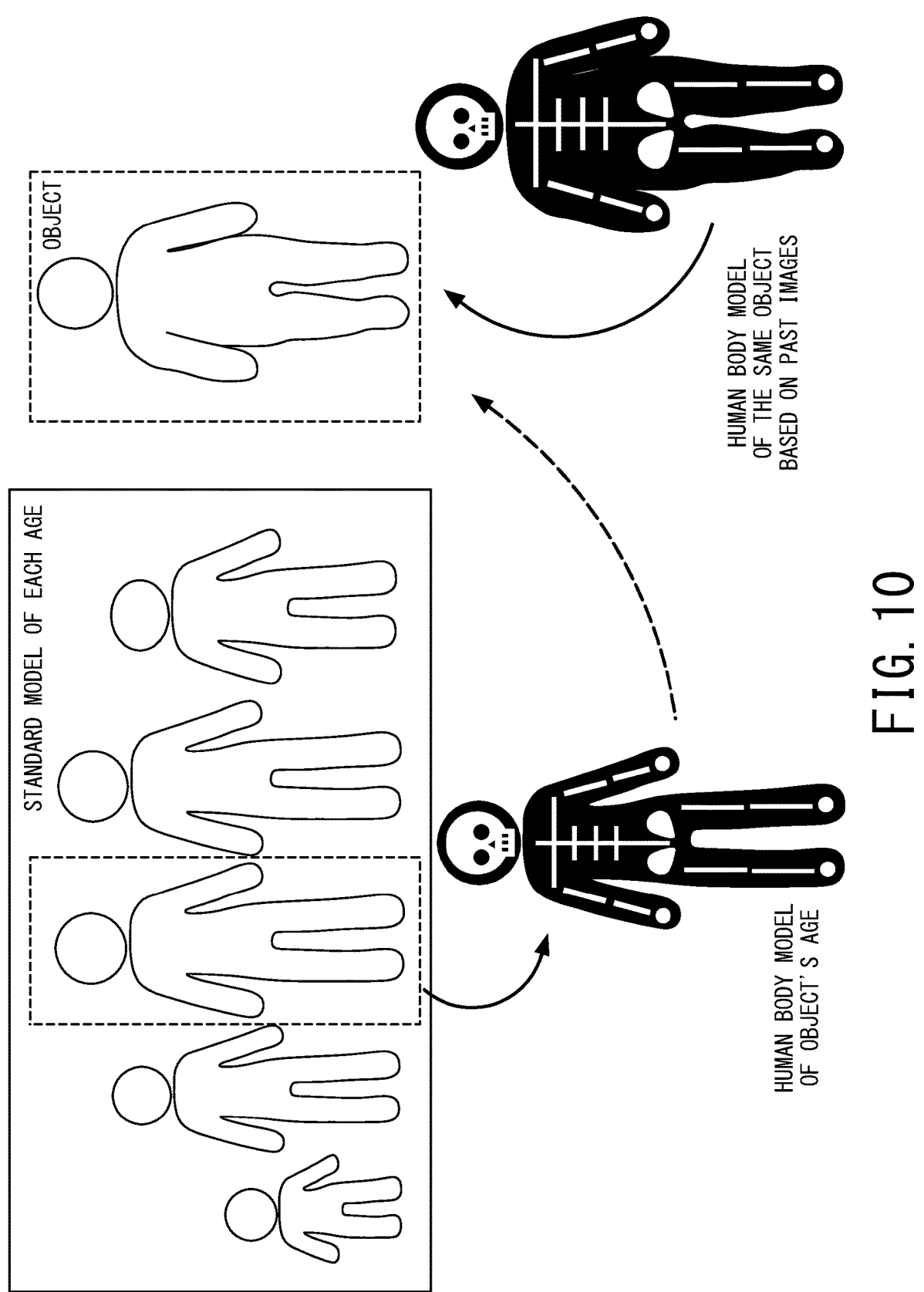
FIG. 10 is a schematic diagram illustrating selection of the human body model according to the modification of the first embodiment.

FIG. 10 is a schematic diagram illustrating selection of a human body model according to the modification of the first embodiment. As shown in FIG. 10, a human body model having the same gender or age of the object P may be selected from the human body models with standard body shapes of each age based on information on the gender and age of the object P obtained from the diagnostic protocol, for example. If there are large individual differences in body size, for example, the human-body-model selection function 315 may select the human body model unique to the object P that is generated from a medical diagnostic image based on diagnosis such as CT and MRI that the same object P has undergone in the past.

Furthermore, the human-body-model selection function 315 may automatically select a human body model that is close to the skeleton or physique of the object P from the camera image (s) generated by the image sensor S. For example, the human-body-model selection function 315 may detect the skeletal or physical characteristics of the object P in terms of height, weight, sitting height, shoulder width, hip width, and/or limb length from the camera image (s) generated by the image sensor S so as to select one human body model close to the skeletal or physical characteristics of the object P from the plurality of human body models that are limited to a special range of values of at least one of its skeletal parameters and physique parameters.

Second Embodiment

Figure 11:
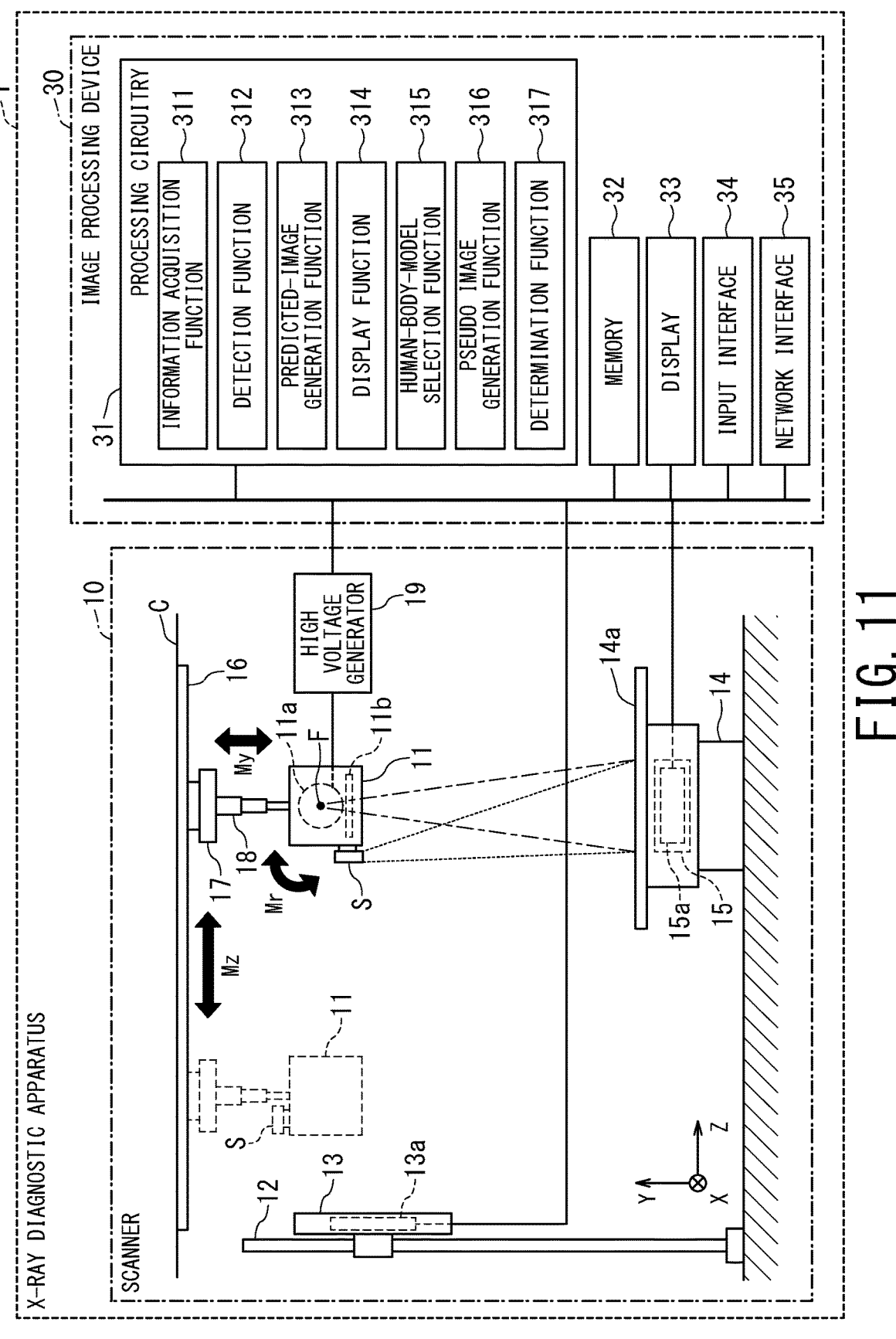
FIG. 11 is a schematic diagram illustrating a configuration of the X-ray diagnostic apparatus according to the second embodiment.

FIG. 11 is a schematic diagram illustrating a configuration of the X-ray diagnostic apparatus 1 according to the second embodiment. As shown in FIG. 11, the second embodiment differs from the first embodiment in that the processing circuitry 31 is further provided with a pseudo-image generation function 316 and a determination function 317.

Figure 12:
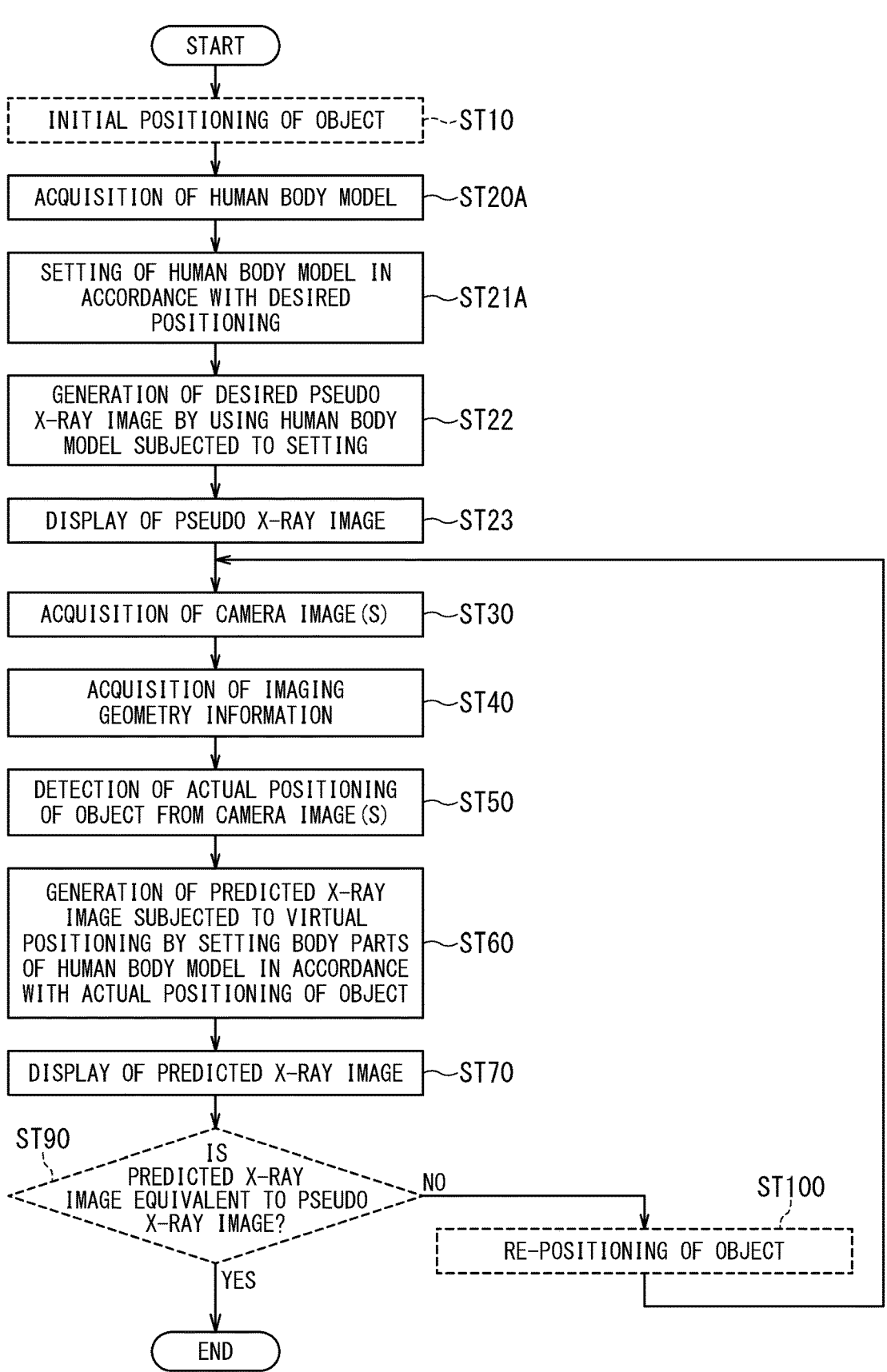
FIG. 12 is a flowchart illustrating operation of the X-ray diagnostic apparatus according to the second embodiment.

FIG. 12 is a flowchart illustrating operation of the X-ray diagnostic apparatus 1 according to the second embodiment.

As shown in FIG. 12, the second embodiment differs from the first embodiment in at least two points as follows. Firstly, in the second embodiment, a two-dimensional pseudo X-ray image is newly generated by setting the body parts of the three-dimensional human model to the desired positioning. Secondly, in the second embodiment, it is determined whether the generated pseudo X-ray image is equivalent to the predicted X-ray image or not. Other configurations and operation are not substantially different from that of the X-ray diagnostic apparatus 1 shown in FIG. 2. Thus, the same reference signs are given to the same configurations, and duplicate description is omitted. The same steps as those in FIG. 5 are denoted by the same reference signs, and duplicate description is omitted.

The processing of the step ST20A is the same as the processing in the first embodiment (FIG. 5).

In the step ST21A, the user sets the body parts of the three-dimensional human body model obtained in the step ST20A in such a manner that the positioning of the human body model matches the desired positioning shown in the X-ray image of the object P to be generated. For example, the user can set the body parts such as bone joints of the human body model to desired positions by operating the mouse and/or another input device of the input interface 34 so as to set the human body model to the desired positioning. The three-dimensional human body model configured to be able to have the body parts set in accordance with the positioning of the object P may include organs and tissues such as skeletons, blood vessels, internal organs, and muscles and may allow organs and tissues other than bones to be moved in conjunction with movement of the bones of the human body model by user's operation.

In the step ST22, on the basis of the imaging geometry information such as the X-ray irradiation angle, the pseudo-image generation function 316 generates a two-dimensional pseudo X-ray image of the object P that has been subjected to virtual positioning from the three-dimensional human body model that is set to match the desired positioning.

In the step ST23, the display function 314 displays the pseudo X-ray image generated by the pseudo-image generation function 316. The pseudo X-ray image is displayed on the operation panel 11c or the display 33, for example. Regarding the display method of the pseudo X-ray image, the pseudo X-ray image may be displayed with only bones, similarly to the display method of the predicted X-ray image. Additionally or alternatively, organs, muscles, and/or blood vessels may be displayed with bones in the pseudo X-ray image, a pseudo X-ray image may be displayed with translucent bones, or a pseudo X-ray image may be displayed with only the outline of the bones.

The processing from the step ST30 to the step ST70 is the same as the processing in the first embodiment (FIG. 5).

In the step ST90, the user determines whether the predicted X-ray image is equivalent to the pseudo X-ray image or not. If the user determines that the predicted X-ray image is equivalent to the pseudo X-ray image (YES in the step ST90), X-ray imaging is performed by the X-ray diagnostic apparatus 1. Conversely, if the user determines that the predicted X-ray image is not equivalent to the pseudo X-ray image (NO in the step ST90), the processing proceeds to the step ST100.

According to the X-ray diagnostic apparatus 1 of the second embodiment, the user can perform repositioning of the object P before X-ray imaging while constantly checking whether the predicted X-ray image is equivalent to the desired pseudo X-ray image or not, and consequently, accuracy of the positioning of the object P can be further enhanced.

Modification of Second Embodiment

Figure 13:
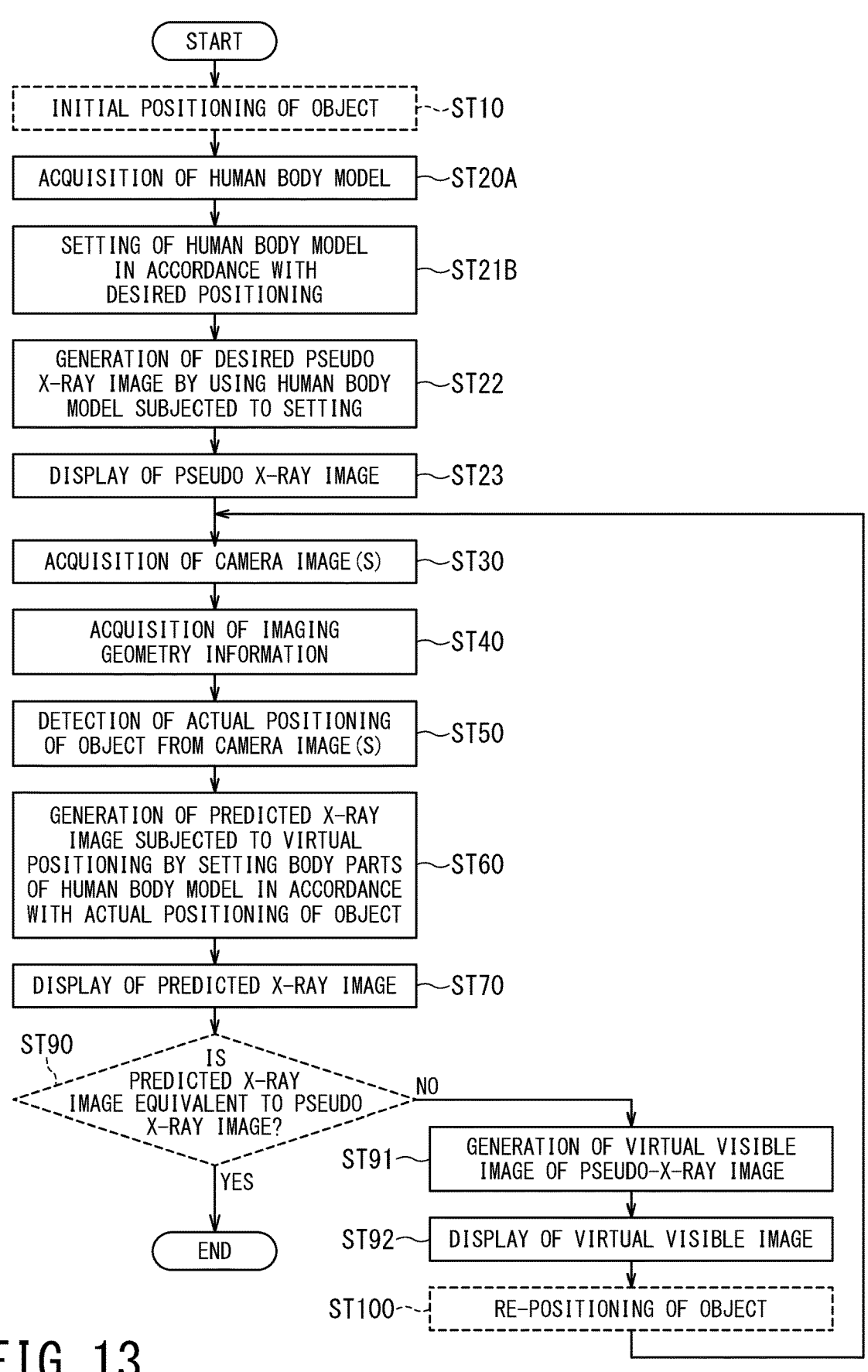
FIG. 13 is a flowchart illustrating operation of the X-ray diagnostic apparatus according to a modification of the second embodiment.

FIG. 13 is a flowchart illustrating operation of the X-ray diagnostic apparatus 1 according to a modification of the second embodiment. Different from the second embodiment where the user performs the processing of setting the human body model in the step ST21A in FIG. 12, in the modification of the second embodiment, the pseudo-image generation function 316 of the processing circuitry 31 performs the processing of setting the human body model in the step ST21B in FIG. 13. The modification of the second embodiment further differs from the second embodiment in that a new step of generating and displaying a virtual visible image of the pseudo X-ray image is executed in order to support the repositioning of the object P. Other configurations and operation are not substantially different from that of the X-ray diagnostic apparatus 1 shown in FIG. 11. Thus, the same reference signs are given to the same configurations, and duplicate description is omitted. The same steps as those in FIG. 12 are denoted by the same reference signs, and duplicate description is omitted.

The processing of the step ST20A is the same as that of the second embodiment (FIG. 12)

In the step ST21B, the pseudo-image generation function 316 acquires information on the examination purpose that is inputted separately, and sets the body parts of the three-dimensional human body model in such a manner that the positioning of the human body model matches the positioning of the object P exemplified in a manual such as an imaging textbook as clinically ideal or standard that is set in the inputted examination purpose. In order to achieve the clinically ideal or standard positioning of the object P, data stored in the memory 32 in advance may be used.

The processing from the step ST22 to step ST70 is the same as the processing of the second embodiment (FIG. 12).

In the step ST90, the determination function determines whether the predicted X-ray image is equivalent to the pseudo X-ray image or not. Known methods for determining image similarity including, for example, application of machine learning. The determination on the predicted X-ray image being equivalent to the pseudo X-ray image may include a certain degree of similarity that is clinically acceptable for the examination.

In the step ST91, on the basis of the pseudo X-ray image, the pseudo-image generation function 316 generates a virtual visible image that supports positioning of the imaging part of the object P.

Figure 14:
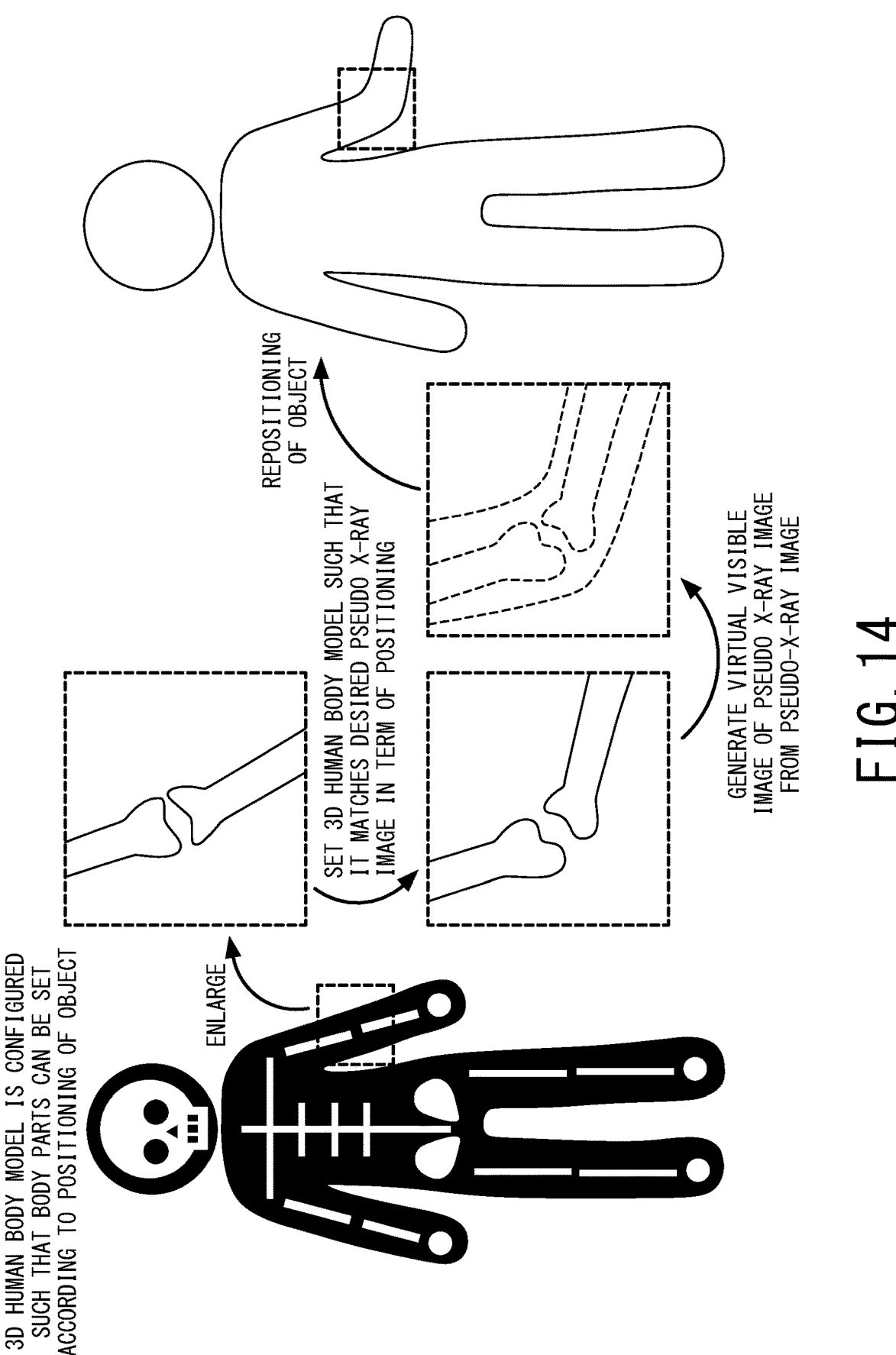
FIG. 14 is a schematic diagram illustrating operation of the X-ray diagnostic apparatus according to the modification of the second embodiment.

FIG. 14 is a schematic diagram illustrating operation of the X-ray diagnostic apparatus 1 according to the modification of the second embodiment. As shown in FIG. 14, the body parts of the three-dimensional human body model are set in such a manner that the positioning of the object P matches the desired positioning, and the desired pseudo X-ray image is generated from the human body model that has been subjected to setting. However, the pseudo X-ray image shows a different appearance from the actual appearance of the object P. Thus, in the step ST91, an image close to the actual appearance of the object P, as exemplified by a virtual visible image of the positioning outline of the object P or a virtual camera image, is generated from the desired pseudo X-ray image as information for supporting the positioning.

In the step ST92, the display function 314 displays the virtual visible image or the virtual camera image generated by the pseudo-image generation function 316. Further, the display function 314 may display the virtual visible image or the virtual camera image together with the pseudo X-ray image, for example. The virtual visible image or the virtual camera image are displayed on the operation panel 11*c* and/or the display 33, for example.

According to the X-ray diagnostic apparatus 1 of the modification of the second embodiment, the virtual visible image or the virtual camera image being close to the actual appearance of object P is displayed, and thus, the user can perform positioning of the object P by referring to the displayed image.

According to at least one embodiment described above, appropriate positioning of an object in accordance with an examination purpose can be supported without increasing the radiation exposure.

In the above-described embodiments, the term "processor" means a circuit such as a special-purpose or general purpose CPU (Central Processing Unit), a GPU (Graphics Processing Unit), an ASIC (Application Specific Integrated Circuit), a programmable logic device including an SPLD (Simple Programmable Logic Device) and a CPLD (Complex Programmable Logic Device), and an FPGA (Field Programmable Gate Array), for example. When the processor is a CPU, for example, the processor implements various functions by reading in and executing the programs stored in the memory.

In addition, when the processor is an ASIC, for example, instead of storing the programs in the memory, the functions corresponding to the programs are directly incorporated in the circuit of the processor as a logic circuit. In this case, the processor implements various functions through hardware processing in which the processor reads in and executes the programs incorporated into the circuit. Additionally or alternatively, the processor can also achieve various functions by combining software processing and hardware processing.

Although a description has been given of the case where a single processor of the processing circuitry 31 achieves the respective functions in the above-described embodiments, the processing circuitry 31 may be configured by combining a plurality of independent processors in such a manner that each processor implements individual function. Further, when a plurality of processors are provided, each processor may be respectively provided with a memory that stores the programs, or a single memory may collectively store the programs corresponding to the functions of all the processors.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the scope of the inventions as defined by the appended claims.

What is claimed is:

1. An X-ray diagnostic apparatus, comprising:
an X-ray tube configured to irradiate an imaging part of an object with X-rays;
an X-ray detector configured to detect the X-rays;
an image sensor configured to image the object; and
processing circuitry configured to
    acquire a human body model, image data from the image sensor, and imaging geometry information,
    detect positioning of the object from the image data,
    set the acquired human body model based on the detected positioning of the object,
    generate a predicted X-ray image that is predicted to be detected by the X-ray detector, by using the set human body model and the acquired imaging geometry information,
    set body parts of the acquired human body model in such a manner that the positioning of the object matches a desired positioning;
    generate a pseudo X-ray image from the human body model that has been subjected to the setting; and
    display at least one of the predicted X-ray image and the pseudo X-ray image.

2. The X-ray diagnostic apparatus according to claim 1, wherein the predicted X-ray image is a predicted X-ray image subjected to virtual positioning by having the body parts of the human body model set to match an actual positioning of the detected object.

3. The X-ray diagnostic apparatus according to claim 1, wherein the predicted X-ray image displayed by the processing circuitry is one of:
an image that depicts only bones;
an image in which at least one of an organ, a muscle, and a blood vessel is depicted together with a bone;
an image that depicts translucent bones; and
an image that depicts only an outline of bones.

4. The X-ray diagnostic apparatus according to claim 1, wherein the processing circuitry is further configured to:
acquire a plurality of human body models; and
select a particular human body model close to a skeleton or a physique of the object from the acquired plurality of human body models.

5. The X-ray diagnostic apparatus according to claim 4, wherein the plurality of human body models is one of:
models with standard body shapes for each gender and each age;
models with characterized body shapes in terms of a skeleton or a physique; and
models generated from medical diagnostic images that were previously acquired.

6. The X-ray diagnostic apparatus according to claim 1, wherein the image sensor is attached to a tube holder configured to hold the X-ray tube in such a manner that the image sensor can image the object in a same direction as an X-ray irradiation direction.

7. The X-ray diagnostic apparatus according to claim 1, wherein the human body model is a three-dimensional human body model configured in such a manner that body parts can be set in accordance with the detected positioning of the object.

8. The X-ray diagnostic apparatus according to claim 7, wherein the processing circuitry is further configured to determine whether or not the predicted X-ray image and the pseudo X-ray image are equivalent to each other.

9. The X-ray diagnostic apparatus according to claim 7, wherein the processing circuitry is further configured to:

use the pseudo X-ray image to generate a virtual visible image or a virtual camera image, each of which supports positioning of an imaging part of the object; and display the virtual visible image or the virtual camera image.

10. The X-ray diagnostic apparatus according to claim 1, wherein the acquired human body model is generated by generative AI from a camera image that is generated by the image sensor.

11. An image processing method, comprising:

acquiring a human body model, image data obtained by imaging an object using an image sensor, and imaging geometry information;

detecting positioning of the object from the image data, setting the acquired human body model based on the detected positioning of the object;

generating a predicted X-ray image that is predicted to be detected by an X-ray detector, by using the human body model and the acquired imaging geometry information;

setting body parts of the acquired human body model in such a manner that the positioning of the object matches a desired positioning;

generating a pseudo X-ray image from the human body model that has been subjected to the setting; and displaying at least one of the predicted X-ray image and the pseudo X-ray image.

12. The image processing method according to claim 11, wherein the predicted X-ray image is a predicted X-ray image subjected to virtual positioning by having the body parts of the human body model set to match an actual positioning of the detected object.

13. The image processing method according to claim 11, wherein the predicted X-ray image is one of:

an image that depicts only bones;

an image in which at least one of an organ, a muscle, and a blood vessel is depicted together with a bone;

an image that depicts translucent bones; and an image that depicts only an outline of bones.

14. The image processing method according to claim 11, further comprising:

acquiring a plurality of human body models; and selecting a particular human body model close to a skeleton or a physique of the object from the acquired plurality of human body models.

15. The image processing method according to claim 14, wherein the plurality of human body models is one of:

models with standard body shapes for each gender and each age;

models with characterized body shapes in terms of a skeleton or a physique; and models generated from medical diagnostic images that were previously acquired.

16. The image processing method according to claim 11, wherein the image sensor is attached to a tube holder configured to hold an X-ray tube in such a manner that the image sensor is configured to image the object in a same direction as an X-ray irradiation direction.

17. The image processing method according to claim 11, wherein the human body model is a three-dimensional human body model configured in such a manner that body parts can be set in accordance with the detected positioning of the object.

18. The image processing method according to claim 17, further comprising determining whether or not the predicted X-ray image and the pseudo X-ray image are equivalent to each other.

19. The image processing method according to claim 17, further comprising:

using the pseudo X-ray image to generate a virtual visible image or a virtual camera image, each of which supports positioning of an imaging part of the object; and displaying the virtual visible image or the virtual camera image.

20. The image processing method according to claim 11, wherein the acquired human body model is generated by generative AI from a camera image that is generated by an image sensor.

* * * * *